United States Patent
Xi et al.

(10) Patent No.: US 9,119,965 B2
(45) Date of Patent: Sep. 1, 2015

(54) SYSTEMS AND METHODS FOR CONTROLLING SPINAL CORD STIMULATION TO IMPROVE STIMULATION EFFICACY FOR USE BY IMPLANTABLE MEDICAL DEVICES

(75) Inventors: Cecilia Qin Xi, San Jose, CA (US); Stuart Rosenberg, Castaic, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 659 days.

(21) Appl. No.: 13/442,749

(22) Filed: Apr. 9, 2012

(65) Prior Publication Data

US 2013/0268016 A1    Oct. 10, 2013

(51) Int. Cl.
- A61N 1/36 (2006.01)
- A61N 1/39 (2006.01)
- A61N 1/368 (2006.01)

(52) U.S. Cl.
CPC .......... *A61N 1/36114* (2013.01); *A61N 1/3684* (2013.01); *A61N 1/36139* (2013.01); *A61N 1/3962* (2013.01)

(58) Field of Classification Search
None
See application file for complete search history.

(56) References Cited

U.S. PATENT DOCUMENTS

| | | | |
|---|---|---|---|
| 6,134,470 A | 10/2000 | Hartlaub | 607/14 |
| 6,480,733 B1 | 11/2002 | Turcott | 600/516 |
| 6,937,896 B1 | 8/2005 | Kroll | 607/9 |
| 7,099,718 B1 | 8/2006 | Thacker et al. | 607/117 |
| 7,162,304 B1 | 1/2007 | Bradley | 607/46 |
| 7,164,944 B1 | 1/2007 | Kroll et al. | 607/2 |
| 7,207,947 B2 | 4/2007 | Koh et al. | 600/529 |
| 7,221,979 B2 | 5/2007 | Zhou et al. | 607/44 |
| 7,650,190 B2 | 1/2010 | Zhou et al. | 607/44 |
| 7,711,415 B1 | 5/2010 | Farazi et al. | 600/509 |
| 7,769,441 B2 | 8/2010 | Foreman et al. | 607/2 |
| 7,826,899 B1 | 11/2010 | Ryu et al. | 607/14 |
| 7,860,563 B2 | 12/2010 | Foreman et al. | 607/2 |

(Continued)

FOREIGN PATENT DOCUMENTS

| | | | | |
|---|---|---|---|---|
| WO | WO 2009/051965 | 4/2009 | | A61N 1/00 |
| WO | WO 2009/058959 | 5/2009 | | A61N 1/20 |

(Continued)

OTHER PUBLICATIONS

McCraty et al., "The Effects of Emotions on Short Term Heart Rate Variability using Power Spectrum Analysis." American Journal of Cardiology. 1995; 76:1089-1093.

*Primary Examiner* — Erica Lee
(74) *Attorney, Agent, or Firm* — Theresa A. Raymer

(57) ABSTRACT

Techniques are provided for controlling spinal cord stimulation (SCS) or other forms of neurostimulation. In one example, SCS treatment is delivered to a patient and nerve impulse firing signals are sensed along the spinal cord following the SCS treatment. The nerve impulse signals are analyzed to determine whether the signals are associated with effective SCS and then the delivery of additional SCS is controlled to improve SCS efficacy. For example, the nerve impulse signals can be analyzed to determine whether the signals are consistent with a positive patient mood associated with pain mitigation and, if not, SCS control parameters are adjusted to improve the efficacy of the SCS in reducing pain. In other examples, heart rate variability (HRV) is also used to control SCS. Still further, adjustments may be made to SCS control parameters to improve antiarrhythmic or sympatholytic effects associated with SCS. Techniques employing baseline/target calibration procedures are also described.

24 Claims, 10 Drawing Sheets

(56) References Cited

U.S. PATENT DOCUMENTS

| | | |
|---|---|---|
| 7,957,797 B2 | 6/2011 | Bourget et al. ............... 607/2 |
| 7,974,693 B2 | 7/2011 | Ben-David et al. .......... 607/17 |
| 2009/0105785 A1 | 4/2009 | Wei et al. ..................... 607/48 |
| 2009/0112283 A1 | 4/2009 | Kriksunov et al. ........... 607/48 |
| 2009/0151737 A1* | 6/2009 | Baxter ......................... 128/898 |
| 2009/0157141 A1 | 6/2009 | Chiao et al. .................. 607/46 |
| 2009/0264783 A1 | 10/2009 | Xi et al. ...................... 600/518 |
| 2009/0281594 A1* | 11/2009 | King et al. ................... 607/46 |
| 2010/0057158 A1 | 3/2010 | Rodriguez et al. ........... 607/22 |
| 2010/0114227 A1 | 5/2010 | Cholette ....................... 607/17 |
| 2010/0114237 A1* | 5/2010 | Giftakis et al. ............... 607/45 |
| 2010/0331921 A1 | 12/2010 | Bornzin et al. ............... 607/62 |
| 2011/0066055 A1 | 3/2011 | Bharmi et al. ............... 600/515 |
| 2011/0137362 A1 | 6/2011 | Foreman et al. ............. 607/14 |
| 2012/0150258 A1* | 6/2012 | Miesel et al. ................. 607/45 |
| 2012/0197336 A1* | 8/2012 | Su ................................. 607/41 |
| 2013/0030490 A1* | 1/2013 | Kornet et al. ................. 607/27 |
| 2013/0106347 A1* | 5/2013 | Kallmyer et al. ............. 320/108 |
| 2013/0144181 A1* | 6/2013 | Fogt et al. .................... 600/521 |

FOREIGN PATENT DOCUMENTS

| | | | | |
|---|---|---|---|---|
| WO | WO 2011/0137193 | | 11/2011 | ............ A61N 1/34 |
| WO | WO 2011/159688 | | 12/2011 | ............ G06K 9/00 |

* cited by examiner

SYSTEMS AND METHODS FOR CONTROLLING SPINAL CORD STIMULATION TO IMPROVE STIMULATION EFFICACY FOR USE BY IMPLANTABLE MEDICAL DEVICES

FIELD OF THE INVENTION

The invention generally relates to implantable medical devices such as pacemakers, implantable cardioverter-defibrillators (ICDs) and spinal cord stimulation (SCS) devices and, in particular, to techniques for controlling SCS based on neural signals, heart rate variability (HRV) or other parameters.

BACKGROUND OF THE INVENTION

SCS is a type of neurostimulation primarily intended to manage chronic pain, particularly within the back, neck, arms or legs. Benefits of SCS or other forms of neurostimulation may include: a reduction in pain; a reduction or elimination of the use of pain medications; and increased activity levels and an improved overall quality of life. Neurostimulation has been used to manage pain that comes from failed back surgery syndrome or post-laminectomy syndrome and other neuropathies. To this end, an SCS system may be implanted within the body to deliver electrical pulses to nerves along the spinal cord. Some patients describe the resulting sensation as a gentle massaging sensation or, in some cases, simply the absence of pain. The SCS system typically includes a small generator device similar to a pacemaker but equipped to send electrical pulses to leads mounted along the nerves near the spinal cord. The generator is usually implanted in the abdomen or buttock area. The stimulation leads may include either thin wires or paddles for delivering electrical pulses to the nerves along the spinal cord. Thin wire leads, also referred to as percutaneous leads, may be implanted within the epidural space. Paddle leads are instead typically implanted during a surgical procedure where a small amount of bone is removed from one of the vertebra. An external controller, similar to a remote control, is provided to allow the patient to control or adjust the neurostimulation.

As such, SCS for chronic pain treatment is essentially a "one way" stimulation system that delivers stimulation with a certain amplitude, pulse width, frequency and duration. The clinician and patient can typically adjust only a few parameters to improve efficacy. There are usually no clear guidelines on what parameters should be adjusted, and by what amount, to improve the SCS. In addition, pain perception can be very subjective. Overtreatment and under-treatment of patients using SCS is also a risk. Perhaps most importantly, conventional SCS systems offer no objective feedback indicative of the efficacy of the stimulation in reducing pain. Still further, the use of SCS for emerging applications, such as an antiarrhythmic therapy or as a sympatholytic agent, may require feedback not based on perceivable pain but rather on objective physiological parameters or measurements. Moreover, issues can arise due to "adaptation," i.e. the same stimulation effective at implant might not be as effective at a later time.

Accordingly, it would be desirable to provide techniques for more objectively assessing the efficacy of SCS and for controlling further SCS to improve stimulation efficacy and aspects of the invention are directed to these ends. Patients with implantable SCS devices may also have implantable cardiac rhythm management (CRM) devices implanted therein such as pacemakers, ICDs or cardiac resynchronization therapy devices (CRTs). Accordingly, it would also be desirable to provide techniques for allowing pacemakers or other devices to measure quantitative parameters within the patient representative of the efficacy of SCS for use in controlling or guiding further SCS therapy. It is to these ends that other aspects of the invention are directed.

SUMMARY OF THE INVENTION

In an exemplary embodiment, a method is provided for use with an implantable system for implant within a patient having an SCS system or other neurostimulation system. Briefly, neurostimulation is delivered to the patient and then spinal cord nerve impulse signals are sensed in response to the neurostimulation. The nerve impulse signals are analyzed to determine whether the signals are indicative of effective neurostimulation. The delivery of additional neurostimulation is then controlled based on the spinal cord nerve signals to adjust and improve neurostimulation efficacy. For example, nerve impulse signals can be analyzed to determine whether the signals are associated with positive patient mood (indicative of successful pain reduction) and, if not, adjustments are to neurostimulation control parameters to improve stimulation efficacy in reducing pain. In other examples, adjustments may be made to improve antiarrhythmic or sympatholytic effects associated with neurostimulation.

In an illustrative implementation, an implantable SCS device is used in conjunction with a pacemaker equipped to analyze spinal cord nerve impulse signals and then control the operation of the SCS device to improve stimulation efficacy by sending appropriate control signals to the SCS device. Exemplary SCS control parameters that may be adjusted by the pacemaker based on the analysis of the nerve impulse signals include: neuromodulation amplitude; neuromodulation frequency; neuromodulation pulse width; and neuromodulation electrode configuration. To sense the nerve impulse signals, the lead system of the SCS may be equipped with suitable sensors for sensing afferent and/or efferent neural electrical signals along spinal cord nerves, such as along a selected dorsal spinal cord fiber. The nerve impulse signals are then forward to the pacemaker for analysis. In one particular example, the system is equipped to sense nerve signals within a passband in the range of 100 Hz to 2 kHz with a sampling frequency of about 4 kHz. To determine whether the sensed nerve impulse signals are indicative of effective SCS, the pacemaker may analyze the signals to determine certain nerve impulse firing parameters or characteristics such as an average firing rate/interval, a maximum/minimum firing rate/interval and firing rate variability (where maximum rate corresponds to minimum interval.) Time-domain nerve impulse signals can be converted to frequency-domain signals so that parameters such as the dominant frequency and its bandwidth can also be determined. This is just an illustrative example and it should be understood that in other implementations the operations performed by the pacemaker could instead be performed by an SCS generator with no pacemaker or by some other device.

In the illustrative implementation where a pacemaker is employed, the pacemaker then compares the nerve impulse firing parameters to pre-determined baseline parameters. In one example, nerve firing parameters are collected or recorded while no SCS is delivered (such as just after implant, not turning on SCS) for use as a baseline, then compared with firing patterns sensed after delivery of SCS stimulation that is known to be effective (e.g. in view of positive moods or emotions) to thereby establish an initial positive therapy "direction" and to establish target firing patterns. The level of effectiveness can be quantified by a positive delta between the initial nerve firing patterns (without SCS) and the subsequent patterns (with SCS.) Similarly, an ineffective or negative direction or delta can be established as well. Later, newly acquired firing patterns are compared to the effective or ineffective patterns or parameters and changes to SCS parameters are made in an effort to achieved target firing patterns. Baseline and target parameters can later be updated as necessary or appropriate. Hence, a determination of effectiveness level can be performed by quantifying the amount of parameter change in the effective direction (positive delta). In other examples, the baseline parameters are associated with SCS that is known to be ineffective. These baseline parameters may be regarded as "negative" or "null" baseline parameters since they are associated with ineffective SCS to be avoided. The various parameters and/or deltas are stored within a memory system of the pacemaker for later comparison against newly-detected nerve impulse parameters. If the newly-detected parameters do not satisfactorily match the positive parameters, adjustments are then made to the SCS control parameters by the pacemaker in an effort to improve the efficacy of the SCS in a positive direction to achieve target nerve impulse firing patterns known to be associated with effective therapy. This procedure may be repeated as needed to adaptively adjust the SCS control parameters.

In some examples, in addition to examining nerve impulse signals, the pacemaker also measures electrical cardiac parameters such as heart rate variability (HRV) and adjusts the SCS control parameters based on those parameters to improve efficacy. In one particular example, the pacemaker measures HRV from an intracardiac electrogram (IEGM) and then assesses a power spectral density (PSD) of HRV to identify target PSD patterns associated with effective SCS (i.e. positive patient mood) or baseline PSD patterns associated with ineffective SCS. As with the nerve impulse parameters, baseline and/or target HRV PSD patterns may be retrieved from memory for comparison against newly-detected HRV PSD patterns. If the newly-detected PSD patterns do not satisfactorily match positive (i.e. target) patterns, adjustments are then made to the SCS control parameters to improve the efficacy of the SCS. Adjustments to SCS made based on HRV may be performed in conjunction with, or separately from, adjustments made based on nerve impulse parameters. Moreover, rather than using a pacemaker, other CRM devices may be used instead such as ICDs or CRTs. Other parameters of HRV may be used instead of or in addition to PSD, including time domain parameters.

In other examples, the SCS device adjusts its own control parameters based on nerve impulse signals (or other suitable parameters indicative of SCS efficacy) such that no pacemaker or other CRM device is needed. In still other examples, an external control system may be used to adjust the operation of the SCS device to improve its efficacy. For example, the external system may receive IEGM data, nerve impulse signal data or other suitable parameters from the implanted devices and then analyze the data to assess the efficacy of the SCS and make adjustments to SCS control parameters, if warranted. Preferably, the patient is also provided with a remote SCS controller for changing the SCS control parameters at his or her discretion.

System and method examples are described in detail below.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable System

Figure 1:
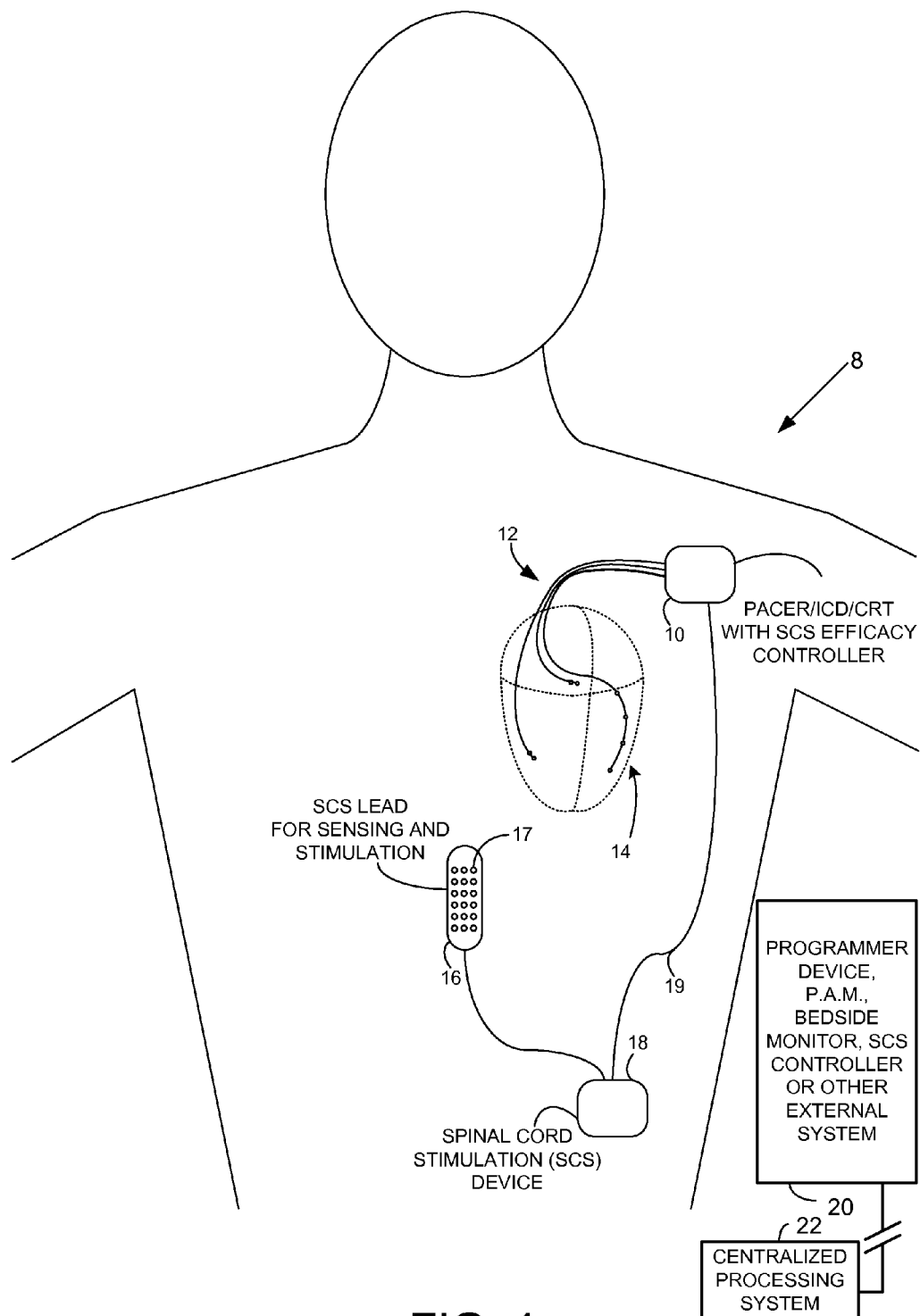
FIG. 1 illustrates pertinent components of an implantable medical system having a pacer/ICD/CRT equipped with an SCS efficacy control system for controlling the operation of an SCS device OR other neurostimulation device.
Figure 8:
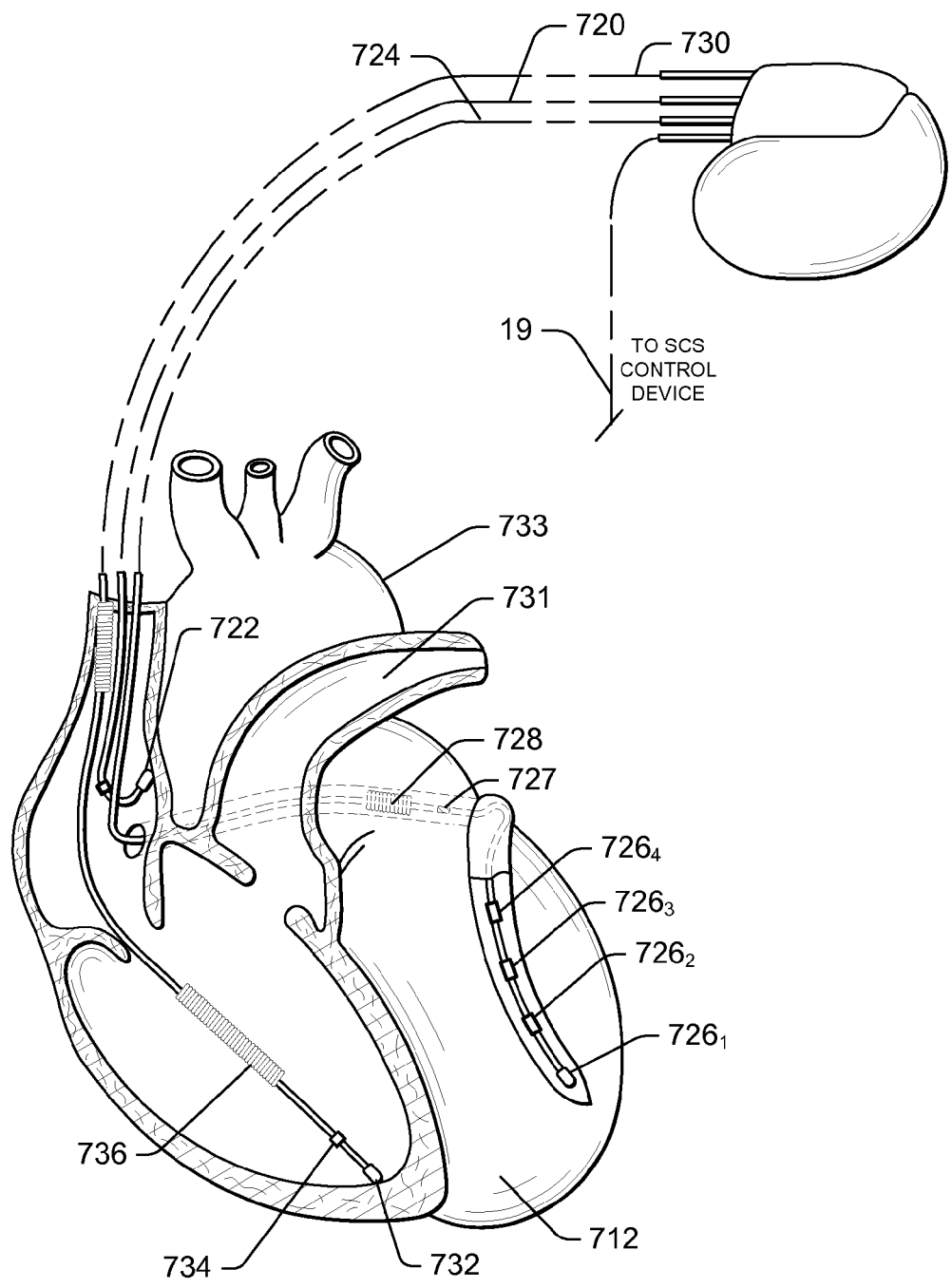
FIG. 8 is a simplified, partly cutaway view of the heart of a patient, illustrating the exemplary pacer/ICD/CRT of FIG. 1, along with a set of leads implanted in the heart of the patient.

FIG. 1 illustrates an implantable medical system 8 having a pacemaker, ICD, CRT or other CRM device 10 equipped to adaptively control SCS or other forms of neurostimulation to improve stimulation efficacy. Herein, for brevity, device 10 will simply be referred to as a pacer/ICD. Control of neurostimulation may be achieved based on an analysis of spinal cord nerve impulse firing parameters, HRV PSD patterns or other suitable parameters. HRV may be assessed based on IEGM signals obtained via a set of leads 12. Three exemplary leads—RA, RV and LV/CS—are shown in FIG. 1 (in stylized form) for sensing IEGM signals. A more complete set of leads is illustrated in FIG. 8, described below. In the example of FIG. 1, the LV/CS lead is a quadripole lead as indicated by a set of four electrodes 14 but other LV lead configurations may be exploited. Spinal cord nerve impulse signals may be sensed by an SCS lead 16 equipped for both sensing and stimulation under the control of an implantable SCS device 18. In the example of FIG. 1, SCS lead 16 is a paddle lead implanted along the lower spine for delivering SCS to nerves in or near the spine while also sensing nerve impulse signals along the same nerves but the lead might be implanted elsewhere in other implementations. Additional SCS leads may be provided. In the example of FIG. 1, the lead has a set of individual electrodes 17 arranged in three columns and six rows for a total of eighteen electrodes. This, of course, is just one example. Also, in other implementations, a separate neural sensing lead may be connected directly to the pacer/ICD. In any case, data and control signals may be communicated between SCS device 18 and pacer/ICD 10 via a connection line or lead 19 or wireless link (not shown.) Also, whereas separate pacer/ICD and SCS devices are shown in the figure, these devices can be merged into a single device that controls both SCS and cardiac rhythm management functions.

In use, pacer/ICD 10 controls implantable SCS device 18 to deliver neurostimulation via lead 16 using a set of neurostimulation control parameters (such as pulse frequency, amplitude, duration, etc.) Data pertaining to nerve impulse signals and/or HRV parameters obtained following the neurostimulation is then analyzed by the pacer/ICD to determine whether the SCS is effective in improving patient mood by reducing pain (or is otherwise having a beneficial effect on the patient.) The pacer/ICD can then make adjustments to the neurostimulation control parameters in an effort to improve SCS by sending suitable control signals to the SCS device. Diagnostic data pertaining to SCS or other functions may be transmitted to an external programmer device, personal advisory module (PAM), bedside monitor, external SCS controller or other external system 20. Additionally, warning signals pertaining to patient health (such as warnings indicating a deterioration of cardiac performance detected by the pacer/ICD) can be transmitted to the external system to alert the patient or caregiver. The external system can forward warning signals or other suitable information via a centralized processing system 22 to the patient's primary care physician or others. The centralized system may include such systems as the HouseCall™ remote monitoring system or the Merlin@home/Merlin.Net systems of St. Jude Medical. Warnings may also be generated using an internal warning device provided within the pacer/ICD. The internal warring device can be a vibrating device or a "tickle" voltage device that, in either case, provides perceptible stimulation to the patient to alert the patient. If equipped with an SCS controller, the external system 20 may allow the patient to transmit control signals directly to the implanted SCS device to override or adjust the neuromodulation control parameters set by the pacer/ICD.

Additionally, the pacer/ICD performs a wide variety of pacing and/or defibrillation functions, such as delivering routine pacing for bradycardia or generating and delivering shocks in response to ventricular fibrillation (VF.) Also, in some examples, the device is equipped to deliver CRT. Briefly, CRT seeks to normalize asynchronous cardiac electrical activation and resultant asynchronous contractions associated with congestive heart failure (CHF) by delivering synchronized pacing stimulus to both ventricles. The stimulus is synchronized so as to improve overall cardiac function. This may have the additional beneficial effect of reducing the susceptibility to life-threatening tachyarrhythmias.

Thus, FIG. 1 provides a broad overview of exemplary systems for controlling SCS or other forms of neurostimulation to improve its efficacy. Embodiments may be implemented that do not necessarily perform all of the described functions. For example, embodiments may be implemented that provide, for example, for controlling neurostimulation but which do not generate and transmit warning signals pertaining to cardiac health. Bedside monitors or PAMs are not necessarily used. Other embodiments might include additional implantable devices or components such as physiological sensors implanted within the heart. These are just a few exemplary embodiments. No attempt is made herein to describe all possible combinations of components that might be provided in accordance with the general principles of the invention. Note also that the particular shapes, sizes and locations of the implanted components shown in FIG. 1 are merely illustrative and may not necessarily correspond to actual implant locations. Preferred implant locations for the leads are more precisely illustrated in FIG. 8. In some cases, rather than interconnecting components via implantable leads, suitable wireless communication systems and channels might be employed. As one example, the neuromodulation control parameters generated by the pacer/ICD might be transmitted to the external system 20, which then relays the signals to implanted SCS device 18 so that interconnection lead 19 is not required. As noted, a pacemaker or other CRMD is not needed. In some examples, the SCS device or controller performs the neurostimulation control functions described herein.

Exemplary Neurostimulation Control Techniques

Figure 2:
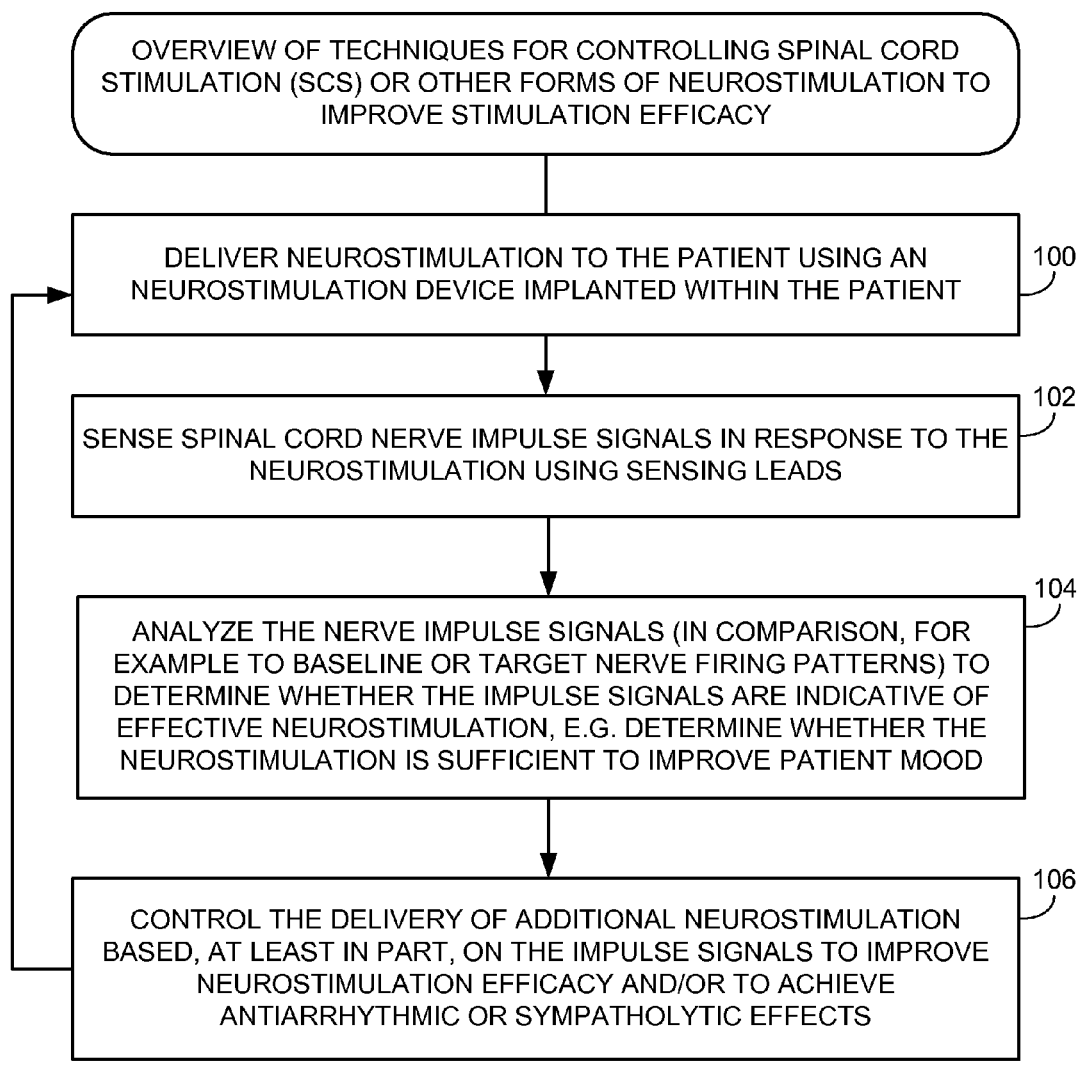
FIG. 2 provides an overview of a method for controlling neurostimulation for use by the system of FIG. 1 wherein neurostimulation is controlled based on spinal cord nerve impulse parameters.

FIG. 2 broadly summarizes the neurostimulation control procedures implement by the system of FIG. 1 or other suitable equipped implantable medical systems, where nerve impulse signals are analyzed. Initially, at step 100, the system delivers neurostimulation to the patient using a neurostimulation device (such as an SCS device) implanted within the patient and, at step 102, the system senses spinal cord nerve impulse signals in response to the neurostimulation using suitable sensing leads. In some examples, the same lead used deliver neurostimulation is also used to sense the nerve impulse signals. In other examples, a separate sensing lead or set of leads is used to sense nerve impulse signals. At step 104, the system analyzes the spinal cord nerve impulse signals (in comparison, for example to baseline nerve firing patterns or target nerve firing patterns as discussed below) to determine whether the signals are associated with effective neurostimulation, e.g. to determine whether the neurostimulation is sufficient to improve patient mood. Various techniques for accomplishing this are described below. Then, at step 106, the system controls the delivery of additional neurostimulation based, at least in part, on the nerve impulse signals to improve stimulation efficacy and/or to achieve beneficial antiarrhythmic or sympatholytic effects. Depending upon the implementation, some of the steps or functions of FIG. 2 may be performed by the pacer/ICD, an implanted SCS device or external systems or components.

Hence, the technique of FIG. 2 advantageously collects neural firing signal characteristics or parameters and analyzes the signal characteristics to guide the neurostimulation system in an effort to achieve optimal pain management results or other desired effects. In this regard, emotion (including response to pain) can affect characteristics of the autonomic nervous system, which can change neural firing signal characteristics. Note that depending upon the location of the neural sensing lead, in some cases a higher frequency neural firing parameter may indicate positive emotions or feelings associated with a reduction in patient pain. In other cases, a lower frequency firing parameter may indicate positive emotions or feelings associated with a reduction in patient pain.

Insofar as neurostimulation for use as an antiarrhythmic therapy or as a sympatholytic agent, such effects may rely on the body's latent physiologic signals (such as nerve firings) rather than on any perceivable pain or other sensation that a patient may qualify or quantify. Hence, adjustments to neurostimulation control parameters based on nerve impulse signals may produce improved antiarrhythmic or sympatholytic treatments. Antiarrhythmic applications of SCS are discussed, for example, in U.S. Patent Application 2011/0137362 of Foreman et al., entitled "Activation of Cardiac Alpha Receptors by Spinal Cord Stimulation Produces Cardioprotection against Ischemia, Arrhythmias, and Heart Failure"; U.S. Pat. No. 6,134,470 to Hartlaub, entitled "Method and Apparatus for Treating a Tachyarrhythmic Patient"; and in U.S. Pat. No. 7,974,693 to Ben-David et al., entitled "Techniques for Applying, Configuring, and Coordinating Nerve Fiber Stimulation." Sympatholytic properties, treatments or agents are discussed, e.g., in U.S. Patent Application 2010/0114227 of Cholette, entitled "Systems and Methods for use by an Implantable Medical Device for Controlling Vagus Nerve Stimulation Based on Heart Rate Reduction Curves and Thresholds to Mitigate Heart Failure" and in U.S. Pat. No. 6,937,896 to Kroll, entitled "Sympathetic Nerve Stimulator and/or Pacemaker." See, also, U.S. Pat. Nos. 7,221,979 and 7,650,190 to Zhou et al., both entitled "Methods and Apparatus for the Regulation of Hormone Release."

Figure 3:
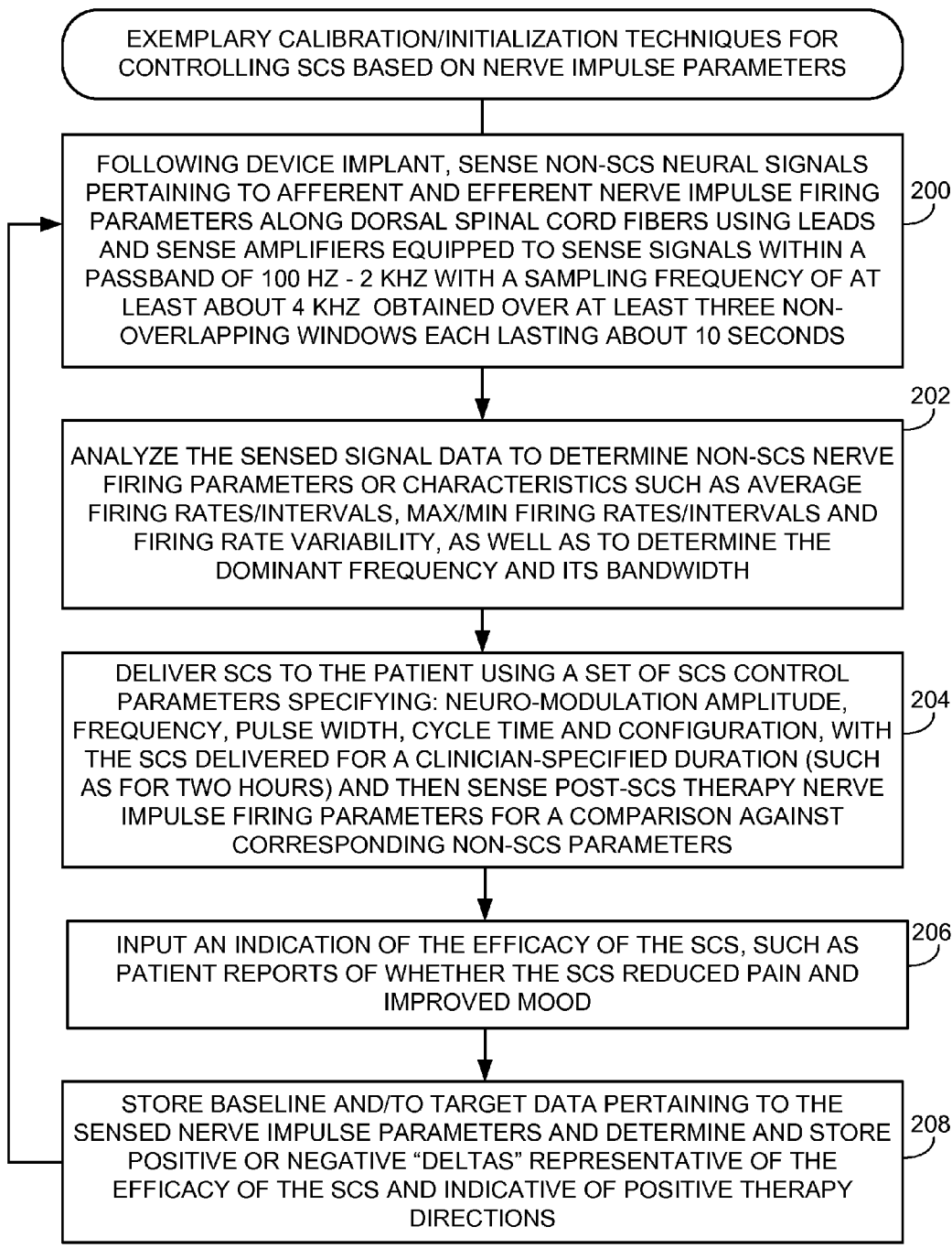
FIG. 3 illustrates an exemplary calibration procedure for use with the general technique of FIG. 2 for determining baseline nerve impulse parameters associated with a lack of effective SCS and target nerve impulse parameters associated with effective SCS.
Figure 4:
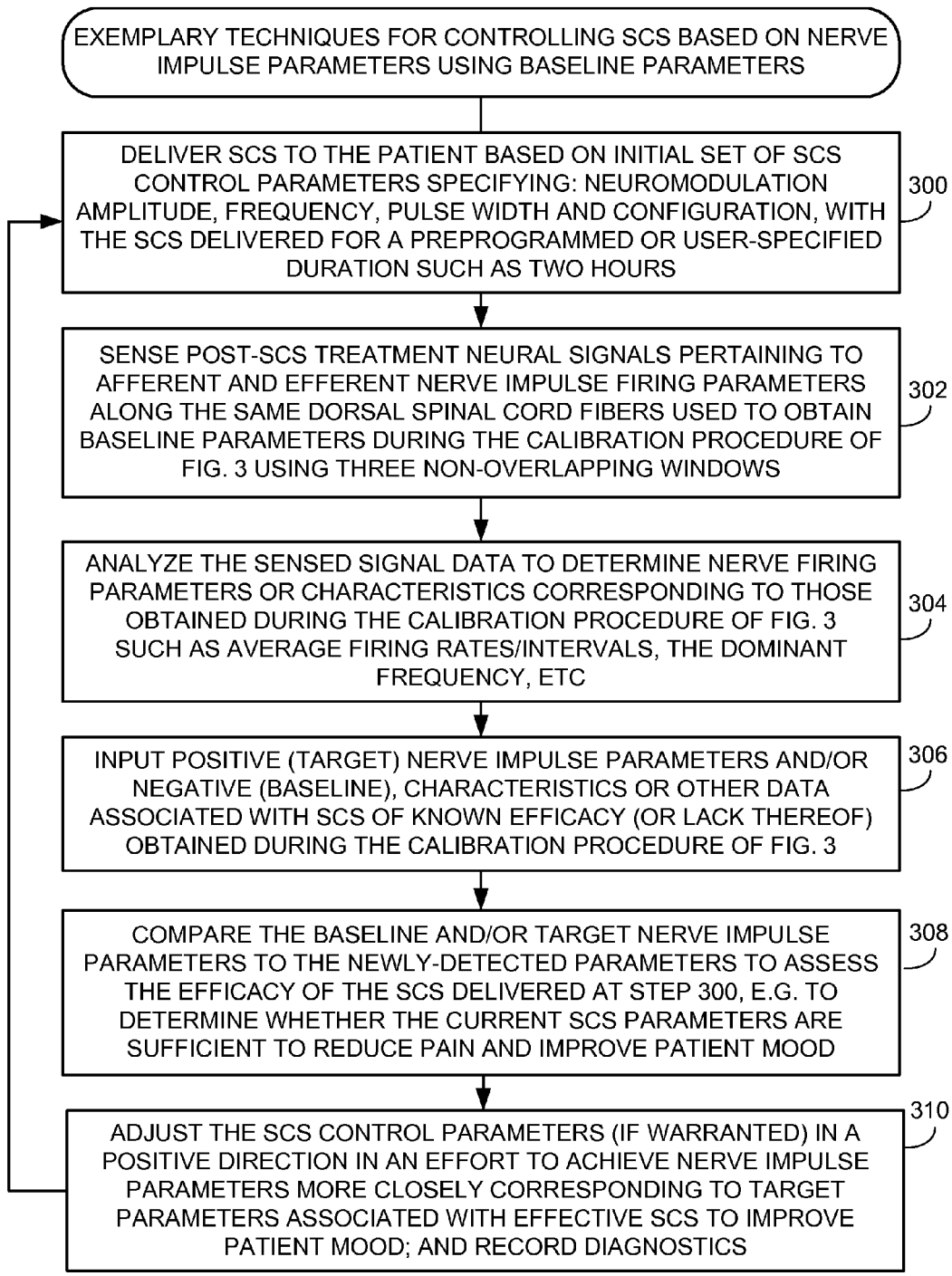
FIG. 4 illustrates an exemplary procedure for use of the general technique of FIG. 2 for comparing newly-detected nerve impulse parameters to baseline and/or target parameters for use in controlling SCS.

Turning now to FIGS. 3 and 4, an illustrative embodiment will be described where SCS is controlled based on nerve impulse parameters to improve patient mood by, for example, reducing pain. Depending upon the implementation, at least some of these steps and functions can be performed by (or controlled by) a pacemaker. In other implementations, at least some of the steps and functions can be performed by (or controlled by) an SCS controller or SCS generator or other device.

FIG. 3 illustrates a calibration or initialization procedure per formed during a post-implant followup session with the clinician to determined and record baseline and/or target nerve impulse parameter data. FIG. 4 illustrates an SCS control procedure that exploits the baseline and/or target data to automatically adjust SCS control parameters, if warranted. Beginning at step 200 of FIG. 3, following device implant, the implantable system uses its implanted leads to sense non-SCS neural signals or parameters pertaining to afferent and efferent nerve impulse parameters along dorsal spinal cord fibers using sense amplifiers equipped to sense signals within a passband of 100 Hz-2 kHz with a sampling frequency of at least about 4 kHz during a period of time in which no SCS is delivered. In order to compensate for neural firing parameter variability during a short window, three non-overlapping windows (e.g., about ten seconds each) can be employed, such that an average of the signal characteristics can then be calculated. Note that accurate neural signal sensing requires good signal to noise ratio, particularly if the neural sensing electrodes are located close to neural stimulation electrodes (or if the same electrodes are used for both sensing and stimulation.) Since the neural signals to be sensed are very low amplitude, a high gain (on the order of 100.times. to 1000.times. amplification) is important, greatly increasing the sensitivity of the sense circuit to noise.

For the sake of completeness, the following descriptions of an exemplary multi-electrode array and sensing circuit are provided. Current SCS stimulation electrodes are typically several millimeters in length and arrayed one to two centimeters apart for percutaneous leads. Surgically implanted "paddle leads" may have various configurations of 2-D arrays but all are typically in the several-millimeter range for electrode size and millimeter-to-centimeter range for inter-electrode spacing. As noted, recording nerve activity within the spinal column typically requires a passband approximately 100 Hz-2 kHz and therefore a sampling frequency of at least 4 kHz. As the signals are very low amplitude, a high gain (i.e. on the order of 100× to 1000× amplification) should be used, greatly increasing the sensitivity of the sense circuit to noise. Individual nerve fibers in the spinal column are on the order of 5-20 microns in diameter and can be very long. However, the fibers have a myelin sheath that acts as an insulator from electrodes located in the epidural space. Thus, it is important to have small electrodes with tight bipolar spacing and high impedance in order to achieve the spatial resolution necessary to distinguish local neural firings.

In one example, a "segmented ring" electrode is implanted in or near the spinal column. The segmented ring is isodiametric with the body of a percutaneous lead (approx 1-2 Fr) and approximately 6 mm long in total. Along the electrode length, the distal and proximal 1.2 mm are each comprised of two small rings 0.5 mm in length and separated by 0.2 mm. The array is separated from the middle remainder of the electrode by approx 0.1 mm. As such, the distal pair of short segments and the proximal pair of short segments are each used for very local sensing of neural activity while the electrode in its entirety is used during stimulation in order to create an electrode of substantial size and intermediate impedance that is appropriate for delivering SCS pulses.

Other sizes for the lead and segmented electrode are of course possible. The overall length of the segmented electrode may be chosen based on matching with conventional percutaneous electrode lengths in order to keep delivery of stimulation consistent with current practice, while the lengths of the distal and proximal segments were chosen in order to provide a very sharply local nerve signal with excellent common mode rejection from other signals such as ambient noise, cardiac signals, myopotentials, etc. However, it may be desirable to use different combinations of overall length, sensing segment length, and bipolar segment spacing, in order to achieve specific objectives such as, for example, distinguishing between (or selectively sensing/rejecting) signals from alpha fibers, beta, fibers, or gamma fibers, or for providing broader or narrower field stimulation within the spinal column. Further, alternately, the sensing segments may be omitted at either the proximal or distal portion of the overall electrode, such that only a single sense pair exists at each electrode, in an effort to minimize the necessary device hardware.

At a sufficiently high sampling frequency, it may be possible to detect a difference in timing between the peak of an activation spike (neural impulse) between the distal and proximal small bipoles. Furthermore, in a multielectrode array of such split-ring electrodes, a timing difference between distal and proximal electrodes on a single lead may also be detectable, especially when considering longer leads and greater distance between distal and proximal electrodes. Employing methods to compare the sequence and timing of distal and proximal spike detections, it is possible to determine whether a signal is afferent or efferent.

While the exemplary electrode just described is intended for a percutaneous spinal cord lead, a similar length and spacing configuration can be applied for flat electrodes on a paddle lead that is implanted by laminotomy procedure. On such paddle lead, it may also be desirable to split the electrode array longitudinally as well, such that bipolar sensing in a lateral orientation (i.e. transverse to the spinal cord axis) can be accomplished. This feature is useful for determining how deep a nerve signal is in the spinal cord. Since neural action potentials will all be of approximately the same amplitude, signals on a transverse bipolar recording electrode will appear larger if they are from the nerve fibers nearby (i.e. more dorsal) and will appear smaller amplitude and of lower frequency content if originating from deeper fibers (i.e. more ventral). The relevance of determining dorsal versus ventral origination is that dorsal spinal cord fibers are typically associated with autonomic and sensory signals while ventral tracts are typically associated with motor signals. Further, it is, of course, advantageous to have multiplexing available (or instead multiple sensing channels that may be simultaneously or selectively recorded.)

At step 202, the implantable system (or an external system in communication therewith) analyzes the signal data sensed at step 200 to determine non-SCS nerve firing parameters or characteristics such as the average firing rate/interval, maximum/minimum firing rate/interval and firing rate variability (where, as noted above, maximum rate corresponds to minimum interval.) Time-domain nerve impulse parameter signals can be converted to frequency-domain signals so that parameters such as the dominant frequency and the bandwidth of dominant frequency can also be determined.

At step 204, the implantable system then delivers SCS to the patient using an implanted SCS lead where the stimulation is controlled based on a set of SCS control parameters specifying: neuromodulation amplitude, neuromodulation frequency, neuromodulation pulse width and neuromodulation configuration and senses post-SCS therapy nerve impulse firing parameters for a comparison against corresponding non-SCS parameters. Exemplary neuromodulation parameters may be set by the clinician in the following ranges: pulse amplitude (0.1-25.5 mA); pulse frequency (2-500 Hz); pulse width (1-1000 μsec); SCS duration (e.g., a few seconds to several hours or other suitable interval of time); and SCS cycle time (e.g. 1 to 6 "doses" per day of a given duration). The neuromodulation configuration may specify, for example, whether a particular SCS electrode is used as an anode or a cathode. SCS stimulation may be delivered, for example, over a period of two hours.

At step 206, the implantable system (or an external system in communication therewith) inputs an indication of the efficacy of the SCS, such as an indication of whether the SCS reduced pain and improved patient mood. For example, the clinician may ask the patient to report the efficacy of the SCS such as whether it successfully reduced pain or generally improved patient mood. The clinician enters the patient's response into a programmer device. However, in some cases, the clinician may know based upon the location of the SCS electrodes whether or not a given firing parameter indicates successful SCS such that patient input is not needed. If so then, following device implant, the clinician specifies the firing parameter characteristics expected to be associated with successful SCS. These firing parameters are selected or otherwise specified by the clinician as the parameters to be achieved by the device via SCS. In this regard, just as a clinician typically knows which IEGM signal parameters are associated with effective cardiac pacing therapy, the clinician may know which neural firing signal parameters are associated with effective SCS and can program the pacer/ICD accordingly.

At step 208, the implantable system stores baseline and/or target data pertaining to nerve impulse parameters and determines and stores positive or negative "deltas" representative of the efficacy of the SCS and/or information pertaining to positive therapy parameter adjustment directions. This data can be relayed to the pace/ICD for storage within its memory. In this manner, the level of effectiveness of the SCS delivered at step 204 can be quantified by a positive or negative delta between the initial nerve firing patterns (without SCS) and the subsequent patterns (with SCS). The overall calibration or initialization procedure may be repeated with other sets of SCS control parameters, particularly if the initial set used at step 200 was not effective in reducing pain and improving patient mood. Note that depending on where the neural sensing electrodes are placed, positive/negative moods or feelings may be associated with increased/decreased nerve firings, or vice versa. Thus, firing patterns or deltas associated with initial untreated states or with ineffective therapies are considered as baseline, whereas firing patterns and deltas associated with effective therapies are considered as targets at the end of the calibration procedure. That is, "baseline" may be regarded in at least some embodiments as referring to the patient's intrinsic activity, which may be in a pathologic state (e.g. refractory pain, poor mood, high arrhythmia burden, etc.) since the patient has the device implanted. Parameters associated with known effective therapy or known good mood are "target" parameters such that the subsequent control to be established by delivering or modifying the neurostimulation parameters seeks to achieve the "target" nerve firing pattern. Hence, the firing patterns associated with a known "good therapy" or state are regarded as "target" parameters while the underlying intrinsic firing associated with a disease or pathological state are regarded as the baseline.

Hence, during the calibration/initialization procedure of FIG. 3, if the patient reports that a particular set of SCS control parameters was effective, the corresponding positive target nerve firing parameters are recorded within the pacer/ICD along with a suitable indication that the parameters correspond to effective SCS. Conversely, if the patient reports the particular set of SCS control parameters were ineffective or adverse, suitable indicators are recoded along with corresponding negative or null baseline nerve firing parameters. As noted, further distinctions can be made based on the relative degree of efficacy, i.e. the relative degree of positive vs. negative patient responses or the delta. In any case, one or more sets of nerve firing parameters are stored within the memory of the pacer/ICD for subsequent use during SCS as baseline parameters.

Turning now to FIG. 4, an SCS control procedure will be described that exploits the baseline and/or target data obtained during the calibration/initialization procedure of FIG. 3 to automatically and adaptively adjust SCS control parameters. Some of the steps of FIG. 4 are similar to those of FIG. 3 and hence will not be described in detail again. Beginning at step 300 of FIG. 4, the implantable system delivers SCS to the patient based on an initial or current set of SCS control parameters. SCS stimulation may be delivered, for example, over a period of two hours, subject to patient control. At step 302, the implantable system senses post-SCS treatment neural signals or parameters pertaining to afferent and efferent nerve impulse parameters along the same dorsal spinal cord fibers used to obtain the baseline parameters of FIG. 3. As with the calibration procedure, three non-overlapping windows may be used for sensing the neural signals, each at least ten seconds in duration, with the data then averaged. At step 304, the implantable system analyzes the sensed signal data to determine nerve firing parameters or characteristics corresponding to those obtained during the calibration procedure of FIG. 3, such as average firing rates/intervals, maximum/minimum firing rate/intervals and firing rate variability, as well as the dominant frequency and its bandwidth.

At step 306, the implantable system inputs the positive target (and/or negative baseline) nerve impulse parameters (recorded during the calibration procedure of FIG. 3) from its memory associated with SCS known to be effective (or known to be ineffective). At step 308, the system compares the baseline and target nerve impulse parameters to the new parameters obtained at step 304 to assess the efficacy of the SCS, e.g. to determine whether the current SCS parameters are sufficient to improve patient mood and reduce pain. For example, the system can assess the numerical difference between the newly-detected parameters (firing rates, etc) and the corresponding baseline or target parameters. A difference (or delta) therebetween may be compared against the delta obtained during calibration (using suitable predetermined threshold values) to determine whether the newly-detected parameters adequately achieve a positive delta (or avoid a negative delta) and hence move therapy in a positive direction so as to achieve target nerve firing patterns known to be effective.

If the newly obtained neural parameters adequately correspond to a positive delta associated with effective (target) SCS, the SCS delivered at step 300 is thereby deemed to be effective and no changes to SCS control parameters are needed. If the newly obtained parameters instead indicate ineffective (baseline) SCS, then the SCS delivered at step 300 is thereby deemed ineffective and adjustments to SCS control parameters are warranted. In some examples, a metric value representing a combination of any or all of these neural parameters may be generated by the device to facilitate comparing the newly obtained parameters with the baseline parameters. Techniques for generating a combined metric based on various parameters for evaluation are discussed in: U.S. Pat. No. 7,207,947 to Koh et al.

At step 310, the implantable system then adjusts the SCS control parameters (if warranted) in a positive direction in an effort to produce nerve impulse parameters within the patient achieving a larger positive delta associated with improved patient mood. In this regard, depending upon the particular implementation, one or more of the neuromodulation control parameters listed above may be adjusted within programmable ranges of values by the pacer/ICD, with the overall procedure repeated until a preferred or optimal set of SCS control parameters is found that yields nerve impulse parameters corresponding to those know to be effective within the patient. In this regard, if the nerve impulse signal characteristics are moved in the positive direction (i.e. SCS yields nerve impulse characteristics more closely associated with advantageous target characteristics), such indicates that the SCS treatment is improving the patient condition. As noted above, in other cases, baseline values indicative of a lack of effective SCS are used and so the procedure instead operates by adjust the SCS control parameters to move the patient away from the baseline.

In any case, by quantifying any change in neural signal characteristics from corresponding baseline and/or target values, the procedure thereby provides a quantitative technique for measuring or assessing the efficacy of the SCS treatment. Patient mood as estimated or assessed by spinal cord neural firings thereby serves as a surrogate or proxy for the degree of pain control afforded with SCS. If a current SCS setting is no longer effective, the sensed signal characteristics will move away from a baseline associated with ineffective SCS and toward target values associated with effective SCS. Thus, by testing other values of the SCS control parameters, for example increasing the amplitude or pulse width to capture more or different nerves in the spinal cord or by changing which electrode configuration is programmed (and measuring the corresponding sensed signal characteristics), the pacer/ICD can determine which set of parameters is most effective. Of course, when considering battery consumption and other factors, a second best option may be chosen instead by the device, based on device programming.

It should be understood that any "optimal" SCS control parameters obtained using techniques described herein are not necessarily absolutely optimal in a mathematical sense. What constitutes "optimal" depends on the criteria used for judging the resulting performance. The SCS control parameters identified or selected using the techniques described herein represent, at least, a "preferred" set of neuromodulation control parameters. Clinicians or patients may choose to adjust or alter the neuromodulation control parameters at their discretion using suitable external control devices. Also, as shown in FIG. 4, the pacer/ICD may record suitable diagnostic information, such as the lists of the SCS parameters selected for subsequent clinician review.

Figure 5:
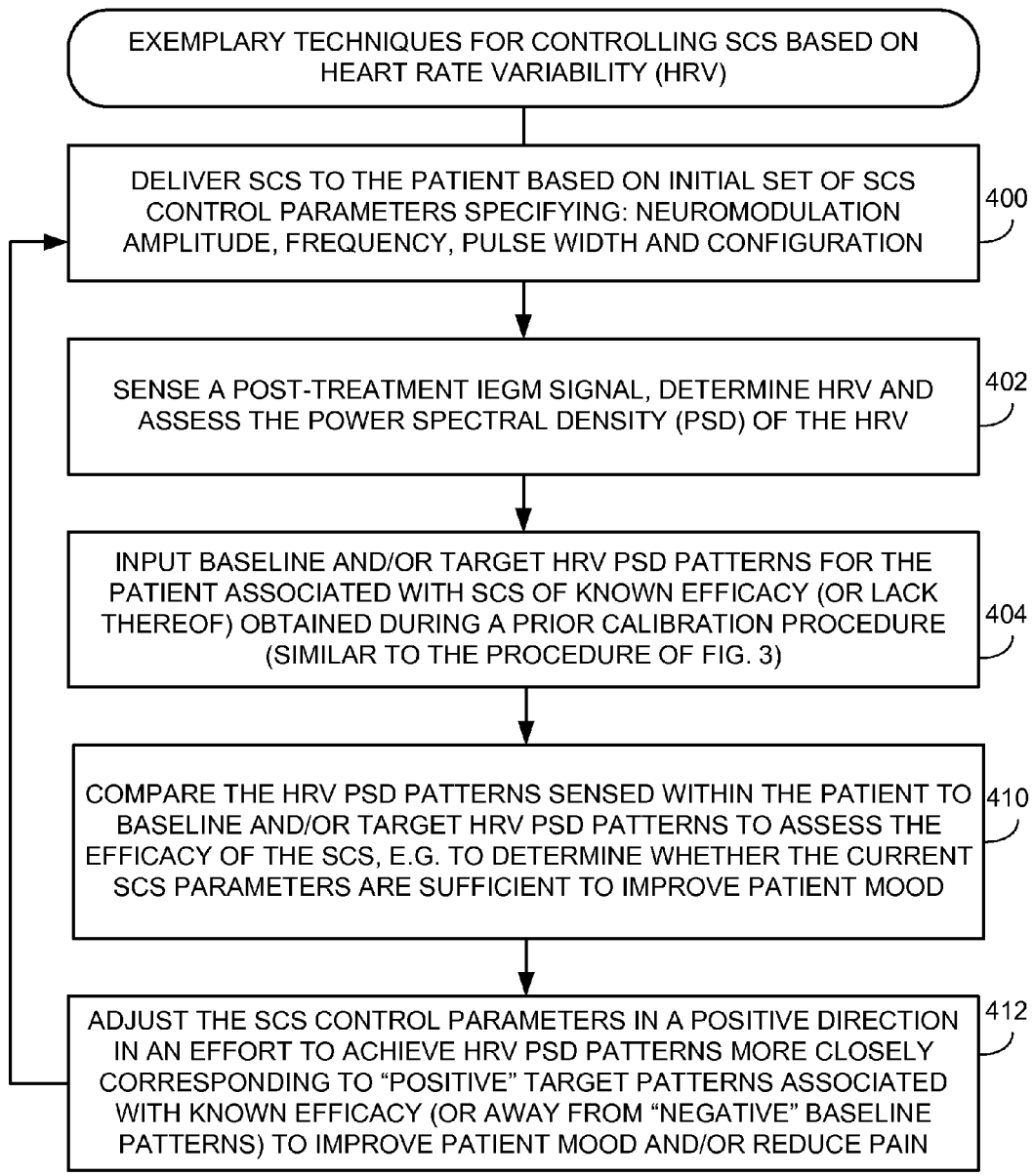
FIG. 5 illustrates an alternative technique for use by the system of FIG. 1 wherein neurostimulation is controlled based on HRV.

FIG. 5 illustrates an alternative SCS control procedure where SCS is controlled based on HRV rather than nerve impulse signals. Some of the steps of FIG. 5 are similar to those of FIG. 4 and hence will not be described in detail again. Beginning at step 400 of FIG. 5, the implantable system delivers SCS to the patient based on initial or current set of SCS control parameters. Again, SCS stimulation may be delivered, for example, over a period of two hours, subject to patient control. At step 402, the implantable system senses post-SCS treatment IEGM signals, determines HRV from the IEGM signals and assess the PSD of the HRV and/or other HRV characteristics. For example, five minutes of IEGM signals may be used to assess HRV. Note that HRV is a physiological phenomenon where the time interval between heartbeats varies and is typically measured as the variation in the beat-to-beat interval. Other terms for HRV may include: "cycle length variability," "RR variability" (where RR is the interval between successive peaks of QRS complexes in the IEGM), and "heart period variability." HRV is discussed in U.S. Patent Application 2009/0264783 to Xi et al., entitled "Systems and Methods for Improved Atrial Fibrillation (AF) Monitoring" and U.S. Pat. No. 6,480,733 to Turcott, entitled "Method for Monitoring Heart Failure."

Herein, the HRV PSD pattern refers to the power spectral density pattern or power spectrum density pattern of HRV. For a discussion of the power spectra of HRV see, for example, U.S. Patent Application 2011/0066055 of Bharmi et al., entitled "System and Method for use with an Implantable Medical Device for Detecting Stroke based on Physiological and Electrocardiac Indices" and U.S. Pat. No. 7,711,415 to Farazi et al., entitled "Implantable Devices, and Methods for use therewith, for Monitoring Sympathetic and Parasympathetic Influences on the Heart." See, also, McCraty et al., "The Effects of Emotions on Short Term Heart Rate Variability using Power Spectrum Analysis." American Journal of Cardiology. 1995; 76:1089-1093.

Figure 6:
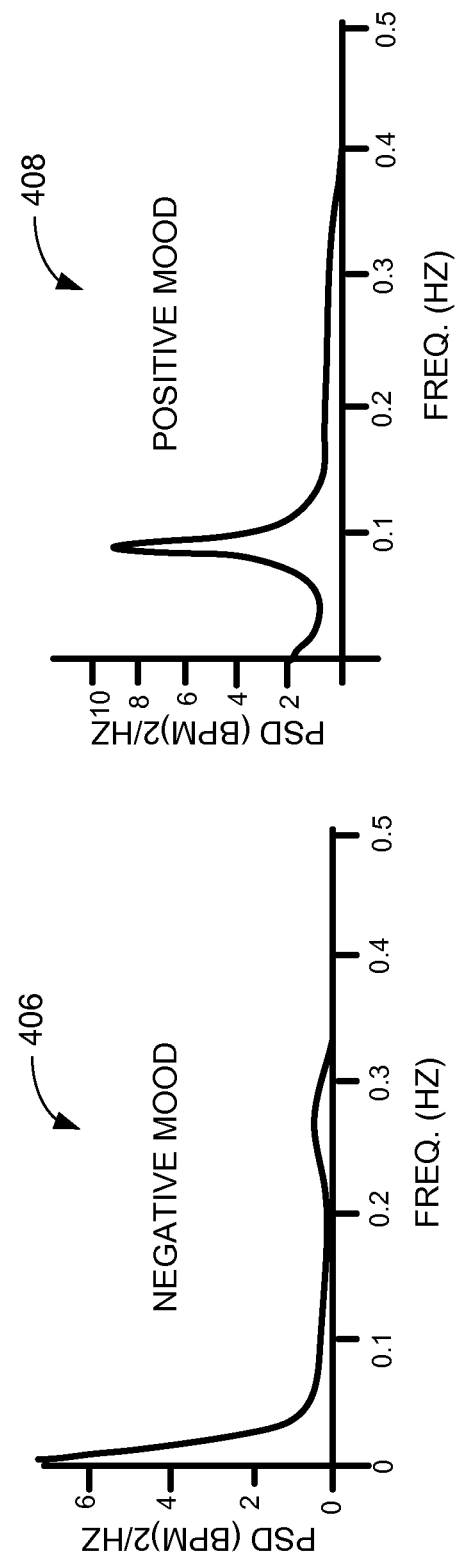
FIG. 6 includes graphs illustrating exemplary HRV PSD patterns exploited by the technique of FIG. 5.

At step 404, the implantable system inputs baseline and/or target HRV PSD parameters for the patient associated with SCS of known efficacy (or lack thereof) obtained during a pervious calibration procedure (similar to the procedure of FIG. 3.) As with the example of FIG. 3 where initially no SCS is delivered, baseline HRV can first be assessed without SCS therapy and then assessed again after SCS has been delivered to determine a positive "delta" in HRV for the patient so as to establish a target HRV pattern. Exemplary HRV PSD patterns are shown in FIG. 6. In particular, a first HRV PSD pattern 406 is representative of the power spectra of HRV associated with a negative baseline mood such as anger, which might arise due to failure of SCS to effectively reduce pain. A second HRV PSD pattern 408 is representative of the power spectra of HRV associated with a positive target mood such as appreciation, as might arise in response to effective SCS. As can be seen, the peak of the power spectra during a positive mood is greater than the peak during a negative mood. Note also that the graphs of FIG. 6 are stylized in the sense that the graphs do not exhibit the sort of noise one expects with actual HRV power spectra.

Returning to FIG. 5, at step 410 the implantable system compares the HRV PSD patterns detected within the patient to the baseline and/or target HRV PSD patterns to assess the efficacy of the SCS, e.g. to determine whether the current SCS parameters are indicative of positive patient mood. For example, numerical parameters may be derived from the HRV PSD patterns for comparison, such as the peak frequency. If the peak frequency of the HRV detected within the patient is more consistent with the peak frequency of the HRV for positive target mood (graph 408 of FIG. 6) rather than negative baseline mood (graph 406 of FIG. 6), the SCS is deemed to be effective and no adjustments to the SCS control parameters are needed. Conversely, if the peak frequency of the HRV detected within the patient is more consistent with the peak frequency of the HRV for negative mood (graph 406 of FIG. 5), the SCS is deemed to be ineffective and adjustments to the SCS control parameters are made.

Accordingly, at step 412, the implantable system then adjusts the SCS control parameters in an effort to achieve HRV PSD patterns more closely corresponding to the positive target patterns associated with positive patient mood and reduced pain and away from negative baseline patterns. Depending upon the particular implementation, one or more of the neuromodulation control parameters described above may be adjusted within its programmable range of values by the pacer/ICD, with the overall procedure repeated until a preferred or optimal set of SCS control parameters is found that improves SCS efficacy.

Figure 7:
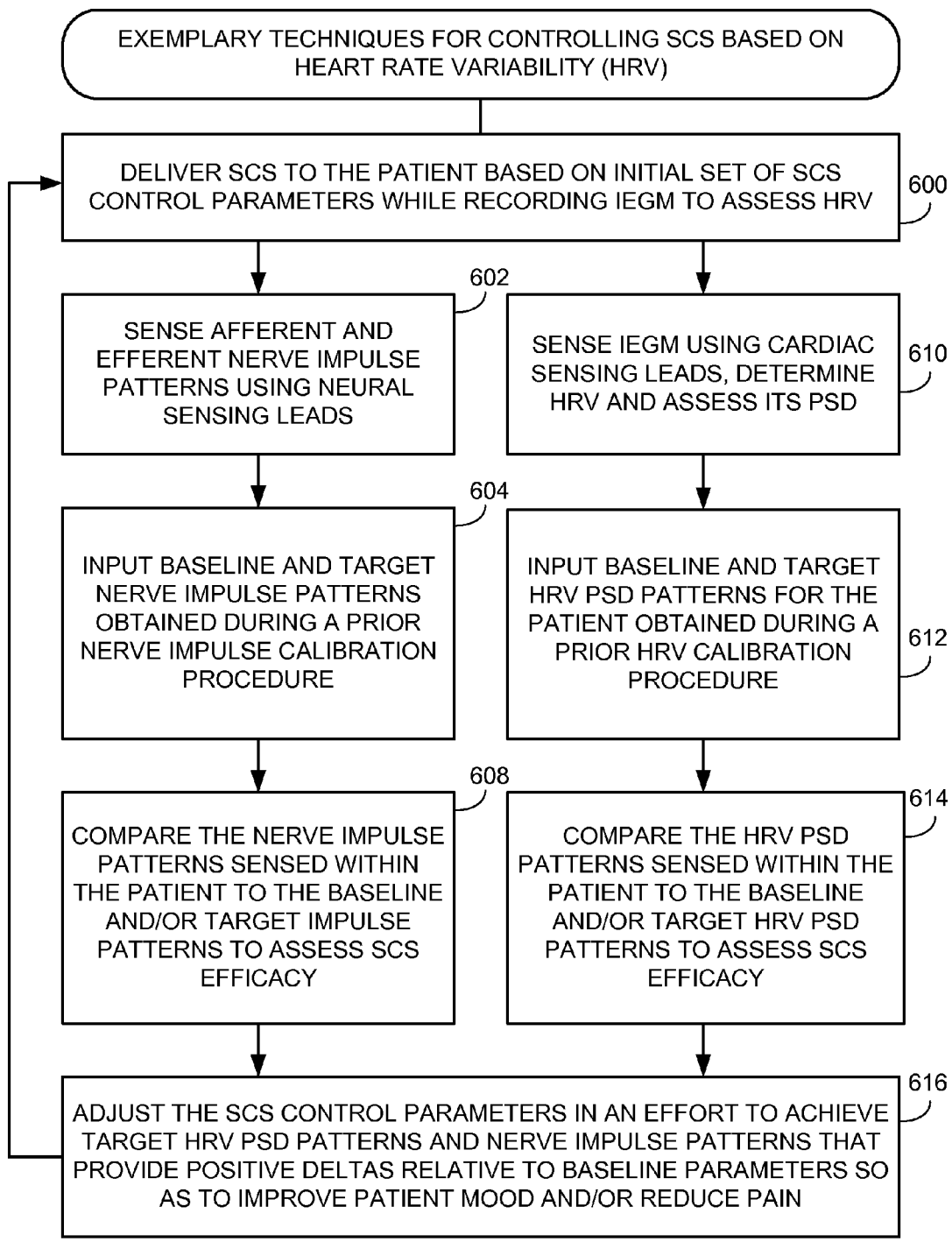
FIG. 7 illustrates yet another alternative technique for use by the system of FIG. 1 wherein SCS is controlled based on nerve impulses and HRV.

As shown in FIG. 7, the neural impulse analysis techniques of FIGS. 3-4 may be combined with the HRV techniques of FIGS. 5-6. Briefly, beginning at step 600 of FIG. 7, the implantable system delivers SCS to the patient based on initial set of SCS control parameters while recording an IEGM to assess HRV. During steps 602, 604 and 608, the pacer/ICD: senses afferent and efferent nerve impulse parameters using sensing leads; inputs baseline and target nerve impulse parameters (or deltas) associated with SCS of known efficacy (or lack thereof) obtained during a prior nerve impulse calibration procedure; and compares the nerve impulse parameters sensed within the patient to the baseline and/or target impulse parameters to assess SCS efficacy. Concurrently, during steps 610, 612 and 614, the pacer/ICD: senses an IEGM using cardiac sensing leads, determines HPV (from the IEGM) and assess its PSD; inputs baseline and target HRV PSD patterns for the patient associated with SCS of known efficacy (or lack thereof) obtained during a prior HRV calibration procedure; and then compares the HRV PSD patterns sensed within the patient to the baseline and/or target HRV PSD patterns to assess SCS efficacy. At step 616, the pacer/ICD then adjusts the SCS control parameters in an effort to achieve target HRV PSD patterns and nerve impulse parameters that that provide positive deltas relative to baseline parameters so as to improve patient mood and/or reduce pain.

What have been described are various neurostimulation control techniques, particularly SCS control techniques. These techniques may be used, where appropriate, in conjunction with other neurostimulation procedures. See, for example, the neurostimulation techniques described in: U.S. Patent Application 2010/0331921 of Bornzin et al., entitled "Neurostimulation Device and Methods for Controlling Same"; U.S. Pat. No. 7,826,899 to Ryu et al. entitled "Neurostimulation and Neurosensing Techniques to Optimize Atrial Anti-Tachycardia Pacing for Termination of Atrial Tachyarrhythmias." See, also, U.S. Patent Application 2010/ 0057158 of Rodriguez et al., entitled "Neurostimulation Based on Glycemic Condition"; U.S. Pat. No. 7,164,944 to Kroll et al., entitled "Analgesic Therapy for ICD Patients." SCS is also discussed, e.g., in U.S. Pat. No. 7,099,718 to Thacker, et al. Techniques for stimulating sympathetic nerves are discussed in U.S. Pat. No. 6,937,896 to Kroll, entitled "Sympathetic Nerve Stimulator and/or Pacemaker."

For the sake of completeness, a pacer/ICD implementation will now be described in detail, which includes components for controlling SCS.

Exemplary Pacer/ICD

Figure 9:
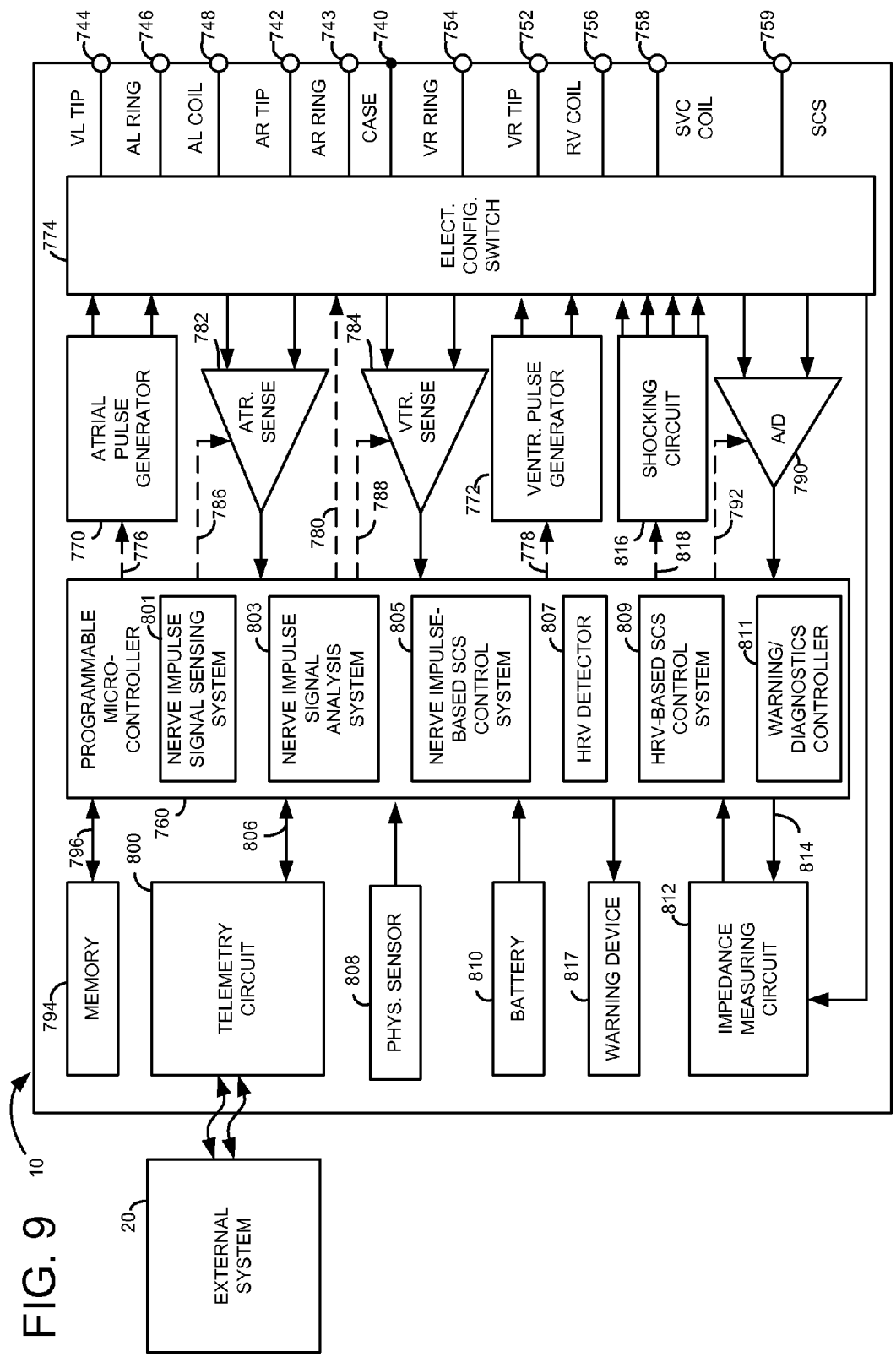
FIG. 9 is a functional block diagram of the pacer/ICD/CRT of FIG. 8, illustrating basic device circuit elements that provide cardioversion, defibrillation and/or pacing stimulation in four chambers of the heart, and particularly illustrating components for controlling neurostimulation.

With reference to FIGS. 8 and 9, a description of an exemplary pacer/ICD will now be provided. FIG. 8 provides a simplified block diagram of the device, which is a dual-chamber stimulation device capable of treating both fast and slow arrhythmias with stimulation therapy, including cardioversion, defibrillation, and pacing stimulation, and also capable of controlling a separate SCS device as discussed above. To provide right atrial chamber pacing stimulation and sensing, device 10 is shown in electrical communication with a heart 712 by way of a right atrial lead 720 having an atrial tip electrode 722 and an atrial ring electrode 723 implanted in the atrial appendage. Device 10 is also in electrical communication with the heart by way of a right ventricular lead 730 having, in this embodiment, a ventricular tip electrode 732, a right ventricular ring electrode 734, a right ventricular (RV) coil electrode 736, and a superior vena cava (SVC) coil electrode 738. Typically, the right ventricular lead 730 is transvenously inserted into the heart so as to place the RV coil electrode 736 in the right ventricular apex, and the SVC coil electrode 738 in the superior vena cava. Accordingly, the RV lead is capable of receiving cardiac signals, and delivering stimulation in the form of pacing and shock therapy to the RV.

To sense left atrial and ventricular cardiac signals and to provide left chamber pacing therapy, device 10 is coupled to a multi-pole LV lead 724 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 724 is designed to receive atrial and ventricular cardiac signals and to deliver left ventricular pacing therapy using a set of four left ventricular electrodes $726_1$, $726_2$, $726_3$, and $726_4$ (thereby providing a quadripole lead), left atrial pacing therapy using at least a left atrial ring electrode 727, and shocking therapy using at least a left atrial coil electrode 728 implanted on or near the left atrium. In other examples, more or fewer LV electrodes are provided. Although only three leads are shown in FIG. 8, it should also be understood that additional leads (with one or more pacing, sensing and/or shocking electrodes) might be used and/or additional electrodes might be provided on the leads already shown.

Additionally, an SCS control lead 19 is provided for connecting the pacer/ICD to one or more neurostimulation control devices such as SCS device 18 of FIG. 1 (or directly to neurostimulation electrodes such as paddle 16 if the pacer/ICD is equipped to directly control neurostimulation.) Note that additional terminal may be required to control neurostimulation depending upon the number of neurostimulation devices and their locations.

A simplified block diagram of internal components of device 10 is shown in FIG. 9. While a particular device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 740 for device 10, shown schematically in FIG. 9, is often referred to as the "can," "case" or "case electrode" and may be programmably selected to act as the return electrode for all "unipolar" modes. The housing 740 may further be used as a return electrode alone or in combination with one or more of the coil electrodes, 728, 736 and 738, for shocking purposes. The housing 740 further includes a connector (not shown) having a plurality of terminals, 742, 743, 744$_1$-744$_4$, 746, 748, 752, 754, 756, 758 and 759 (shown schematically and, for convenience, the names of the electrodes to which they are connected are shown next to the terminals). As such, to achieve right atrial sensing and pacing, the connector includes at least a right atrial tip terminal ($A_R$ TIP) 742 adapted for connection to the atrial tip electrode 722 and a right atrial ring ($A_R$ RING) electrode 743 adapted for connection to right atrial ring electrode 723. To achieve left chamber sensing, pacing and shocking, the connector includes a left ventricular tip terminal (VL$_1$ TIP) 744$_1$ and additional LV electrode terminals 744$_2$-744$_4$ for the other LV electrodes of the quadripole LV lead. A terminal 759 is shown for connection to SCS control lead 19. Depending upon the particular SCS system, additional terminals may be needed.

The connector also includes a left atrial ring terminal ($A_L$ RING) 746 and a left atrial shocking terminal ($A_L$ COIL) 748, which are adapted for connection to the left atrial ring electrode 727 and the left atrial coil electrode 728, respectively. To support right chamber sensing, pacing and shocking, the connector further includes a right ventricular tip terminal ($V_R$ TIP) 752, a right ventricular ring terminal ($V_R$ RING) 754, a right ventricular shocking terminal ($V_R$ COIL) 756, and an SVC shocking terminal (SVC COIL) 758, which are adapted for connection to the right ventricular tip electrode 732, right ventricular ring electrode 734, the $V_R$ coil electrode 736, and the SVC coil electrode 738, respectively.

At the core of pacer/ICD 10 is a programmable microcontroller 760, which controls the various modes of stimulation therapy. As is well known in the art, the microcontroller 760 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 760 includes the ability to process or monitor input signals (data) as controlled by a program code stored in a designated block of memory. The details of the design and operation of the microcontroller 760 are not critical to the invention. Rather, any suitable microcontroller 760 may be used that carries out the functions described herein. The use of microprocessor-based control circuits for performing timing and data analysis functions are well known in the art.

As shown in FIG. 9, an atrial pulse generator 770 and a ventricular pulse generator 772 generate pacing stimulation pulses for delivery by the right atrial lead 720, the right ventricular lead 730, and/or the CS lead 724 via an electrode configuration switch 774. It is understood that in order to provide stimulation therapy in each of the four chambers of the heart, the atrial and ventricular pulse generators, 770 and 772, may include dedicated, independent pulse generators, multiplexed pulse generators or shared pulse generators. The pulse generators, 770 and 772, are controlled by the microcontroller 760 via appropriate control signals, 776 and 778, respectively, to trigger or inhibit the stimulation pulses.

The microcontroller 760 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 774 includes a plurality of switches for connecting the desired electrodes to the appropriate I/O circuits, thereby providing complete electrode programmability. Accordingly, the switch 774, in response to a control signal 780 from the microcontroller 760, determines the polarity of the stimulation pulses (e.g., unipolar, bipolar, combipolar, etc.) by selectively closing the appropriate combination of switches (not shown) as is known in the art.

Atrial sensing circuits 782 and ventricular sensing circuits 784 may also be selectively coupled to the right atrial lead 720, CS lead 724, and the right ventricular lead 730, through the switch 774 for detecting the presence of cardiac activity in each of the four chambers of the heart. Accordingly, the atrial (ATR. SENSE) and ventricular (VTR. SENSE) sensing circuits, 782 and 784, may include dedicated sense amplifiers, multiplexed amplifiers or shared amplifiers. The switch 774 determines the "sensing polarity" of the cardiac signal by selectively closing the appropriate switches, as is also known in the art. In this way, the clinician may program the sensing polarity independent of the stimulation polarity. Each sensing circuit, 782 and 784, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 782 and 784, are connected to the microcontroller 760 which, in turn, are able to trigger or inhibit the atrial and ventricular pulse generators, 770 and 772, respectively, in a demand fashion in response to the absence or presence of cardiac activity in the appropriate chambers of the heart.

For arrhythmia detection, pacer/ICD 10 utilizes the atrial and ventricular sensing circuits, 782 and 784, to sense cardiac signals to determine whether a rhythm is physiologic or pathologic. As used in this section, "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 760 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 790. The data acquisition system 790 is configured to acquire intracardiac electrogram signals, convert the raw analog data into a digital signal, and store the digital signals for later processing and/or telemetric transmission to an external device 16. The data acquisition system 790 is coupled to the right atrial lead 720, the CS/LV lead 724, and the right ventricular lead 730 through the switch 774 to sample cardiac signals across any pair of desired electrodes. The microcontroller 760 is further coupled to a memory 794 by a suitable data/address bus 796, wherein the programmable operating parameters used by the microcontroller 760 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 794 through a telemetry circuit 800 in telemetric communication with the external device 20, such as a programmer, transtelephonic transceiver, a diagnostic system analyzer, bedside monitor or PAM. The telemetry circuit 800 is activated by the microcontroller by a control signal 806. The telemetry circuit 800 advantageously allows intracardiac electrograms and status information relating to the operation of pacer/ICD 10 (as contained in the microcontroller 760 or memory 794) to be sent to the external device 20 through an established communication link 804.

Pacer/ICD 10 further includes an accelerometer or other physiologic sensor or sensors 808, sometimes referred to as a "rate-responsive" sensor because it is typically used to adjust pacing stimulation rate according to the exercise state of the patient. However, physiological sensor(s) 808 can be equipped to sense any of a variety of cardiomechanical parameters, such as heart sounds, systemic pressure, etc. As can be appreciated, at least some these sensors may be mounted outside of the housing of the device and, in many cases, will be mounted to the leads of the device. Moreover, the physiological sensor 808 may further be used to detect changes in cardiac output, changes in the physiological condition of the heart, or diurnal changes in activity (e.g., detecting sleep and wake states) and to detect arousal from sleep. Accordingly, the microcontroller 760 responds by adjusting the various pacing parameters (such as rate, AV delay, V-V delay, etc.) at which the atrial and ventricular pulse generators, 770 and 772, generate stimulation pulses. While shown as being included within pacer/ICD 10, it is to be understood that the physiologic sensor 808 may also be external to pacer/ICD 10, yet still be implanted within or carried by the patient. A common type of rate responsive sensor is an activity sensor incorporating an accelerometer or a piezoelectric crystal and/or a 3D-accelerometer capable of determining patient posture, which is mounted within the housing 740 of pacer/ICD 10. Other types of physiologic sensors are also known, for example, sensors that sense the blood oxygen content, respiration rate and/or minute ventilation, blood pH, ventricular gradient, etc.

The pacer/ICD additionally includes a battery 810, which provides operating power to all of the circuits shown in FIG. 9. The battery 810 may vary depending on the capabilities of pacer/ICD 10. If the system only provides low voltage therapy, a lithium iodine or lithium copper fluoride cell typically may be utilized. For pacer/ICD 10, which employs shocking therapy, the battery 810 should be capable of operating at low current drains for long periods, and then be capable of providing high-current pulses (for capacitor charging) when the patient requires a shock pulse. The battery 810 should also have a predictable discharge characteristic so that elective replacement time can be detected. Accordingly, appropriate batteries are employed.

As further shown in FIG. 9, pacer/ICD 10 is shown as having an impedance measuring circuit 812, which is enabled by the microcontroller 760 via a control signal 814. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 812 is advantageously coupled to the switch 874 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 760 further controls a shocking circuit 816 by way of a control signal 818. The shocking circuit 816 generates shocking pulses of low (up to 0.5 joules), moderate (0.5-10 joules) or high energy (11 to 40 joules or more), as controlled by the microcontroller 760. Such shocking pulses are applied to the heart of the patient through at least two shocking electrodes, and as shown in this embodiment, selected from the left atrial coil electrode 728, the RV coil electrode 736, and/or the SVC coil electrode 738. The housing 740 may act as an active electrode in combination with the RV electrode 736, or as part of a split electrical vector using the SVC coil electrode 738 or the left atrial coil electrode 728 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 10-40 joules or more), delivered asynchronously (since R-waves may be too disorganized), and pertaining exclusively to the treatment of fibrillation. Accordingly, the microcontroller 760 is capable of controlling the synchronous or asynchronous delivery of the shocking pulses.

Insofar as neurostimulation is concerned, the microcontroller includes a nerve impulse signal sensing system 801 operative to sense spinal cord nerve impulse signals and parameters in response to the SCS. Depending upon the particular implementation, sensing system 801 may receive the signals via lead 19 (FIG. 1) from a separate SCS device or, if equipped with a suitable neural sensing lead, the pacer/ICD may directly receive the signals. A nerve impulse signal analysis system 803 is operative to analyze the nerve impulse signals and parameters to determine whether the impulse signals are associated with effective SCS. A nerve impulse-based SCS control system 805 is operative to control the delivery of additional SCS based, at least in part, on the nerve impulse signal so as to improve SCS efficacy. An HRV detector 807 is also provided to detect, measure or assess the HRV of the patient (based on IEGM signals sensed via sense amplifier 784.) An HRV-based SCS control system 809 controls the delivery of additional SCS based, at least in part, on HRV so as to improve SCS efficacy. Individually or collectively, never impulse-based SCS control system 805 and HRV-based SCS control system 809 provides an SCS control system operative to control the delivery of SCS. SCS control signals may be sent via lead 19 to the SCS device (FIG. 1), which then controls delivery of SCS to the patient. As noted, in some examples, rather than having an SCS system implanted separately from the pacer/ICD, the pacer/ICD directly controls one or more SCS leads (such as paddle lead 16 of FIG. 1) via SCS terminal 759. Any diagnostic data pertinent to SCS, cardiac health or other matters can be stored in memory 794 under the control of diagnostic controller 811 for eventual transmission to an external system. Controller 811 also controls the generation of warning signals via warning device 817.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like. Also, it should be understood that at least some of the procedures or functions described herein might be performed by a device external to the patient, such as a bedside monitor or device programmer, based on data or signals transmitted from the implanted system.

As noted, at least some of the techniques described herein can be performed by (or under the control of) an external device. For the sake of completeness, a detailed description of an exemplary programmer is provided.

Exemplary External Programmer

Figure 10:
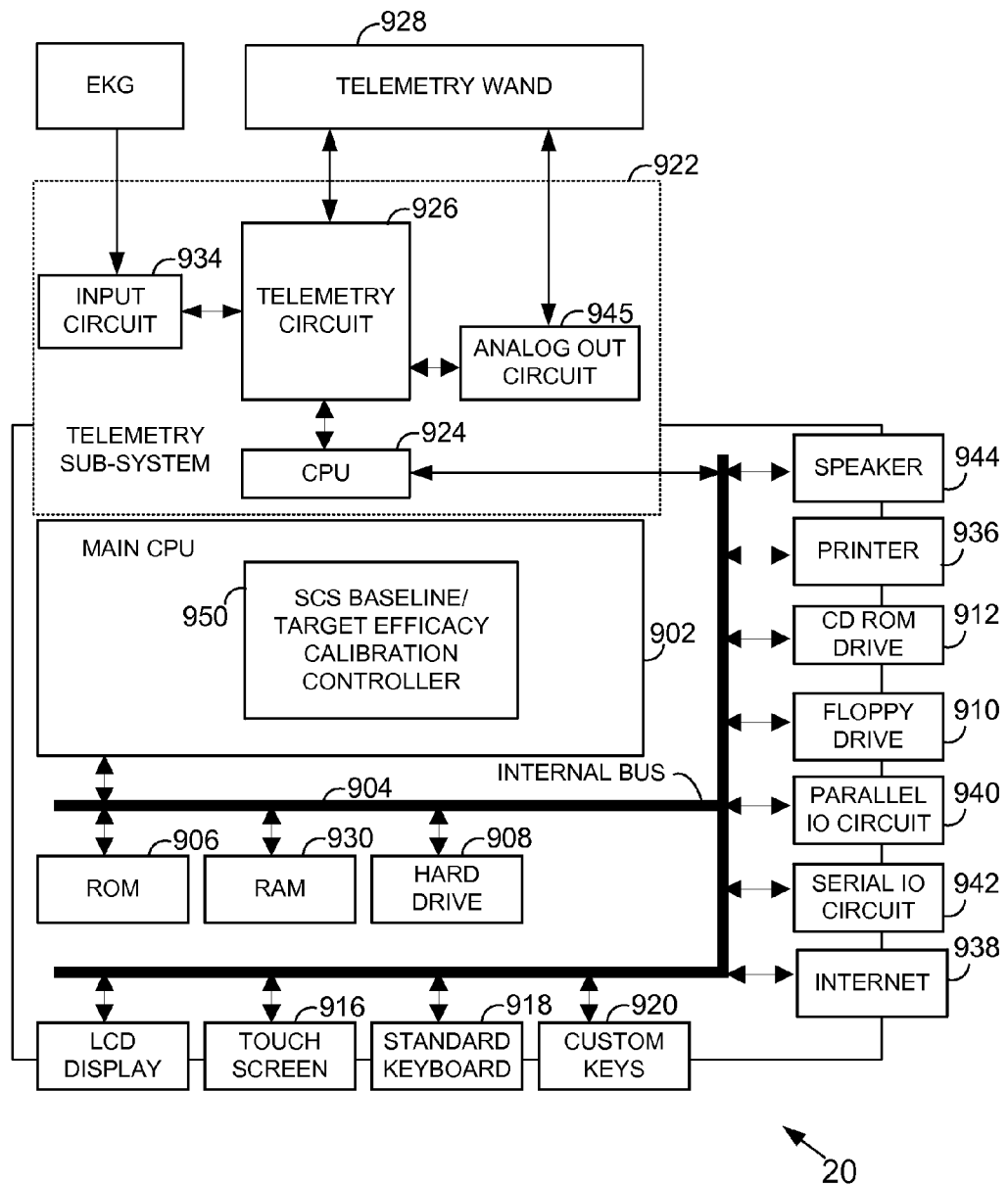
FIG. 10 is a functional block diagram illustrating components of the external programmer of FIG. 1, particularly illustrating programmer-based components for controlling the neurostimulation calibration techniques.

FIG. 10 illustrates pertinent components of an external programmer 20 for use in programming the pacer/ICD of FIGS. 8 and 9 and for performing the above-described SCS calibration techniques. For the sake of completeness, other device programming functions are also described herein. Generally, the programmer permits a physician, clinician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 20 may also be capable of processing and analyzing data received from the implanted device and from the EKG leads to, for example, render preliminary diagnosis as to medical conditions of the patient or to the operations of the implanted device.

Now, considering the components of programmer 20, operations of the programmer are controlled by a CPU 902, which may be a generally programmable microprocessor or microcontroller or may be a dedicated processing device such as an application specific integrated circuit (ASIC) or the like. Software instructions to be performed by the CPU are accessed via an internal bus 904 from a read only memory (ROM) 906 and random access memory 930. Additional software may be accessed from a hard drive 908, floppy drive 910, and CD ROM drive 912, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 914 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 916 overlaid on the LCD display or through a standard keyboard 918 supplemented by additional custom keys 920, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 20 to retrieve data stored within any implanted devices and to also retrieve EKG data from EKG leads, if any, coupled to the patient. To this end, CPU 902 transmits appropriate signals to a telemetry subsystem 922, which provides components for directly interfacing with the implanted devices, and the EKG leads. Telemetry subsystem 922 includes its own separate CPU 924 for coordinating the operations of the telemetry subsystem. Main CPU 902 of programmer communicates with telemetry subsystem CPU 924 via internal bus 904. Telemetry subsystem additionally includes a telemetry circuit 926 connected to telemetry wand 928, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an input circuit 934 for receiving surface EKG signals from a surface EKG system 932. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the CRT device also includes the data stored within the recalibration database of the CRT device (assuming the CRT device is equipped to store that data.) Data retrieved from the implanted devices is stored by external programmer 20 either within a random access memory (RAM) 930, hard drive 908 or within a floppy diskette placed within floppy drive 910. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 20, the implanted devices may be further controlled to transmit additional data in real time as it is detected by the implanted devices, such as additional IEGM data, lead impedance data, and the like. Additionally, or in the alternative, telemetry subsystem 922 receives EKG signals from EKG leads 932 via an EKG processing circuit 934. As with data retrieved from the implanted device itself, signals received from the EKG leads are stored within one or more of the storage devices of the external programmer. Typically, EKG leads output analog electrical signals representative of the EKG. Accordingly, EKG circuit 934 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 902, the programming commands are converted to specific programmable parameters for transmission to the implanted devices via telemetry wand 928 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 936.

Programmer/monitor 20 also includes an internet connection 938 to permit direct transmission of data to other programmers via the public switched telephone network (PSTN) or other interconnection line, such as a T1 line, fiber optic cable, Wi-Fi, cellular network, etc. Depending upon the implementation, the modem may be connected directly to internal bus 904 may be connected to the internal bus via either a parallel port 940 or a serial port 942. Other peripheral devices may be connected to the external programmer via parallel port 940 or a serial port 942 as well. Although one of each is shown, a plurality of input output (IO) ports might be provided. A speaker 944 is included for providing audible tones to the user, such as a warning beep in the event improper input is provided by the physician. Telemetry subsystem 922 additionally includes an analog output circuit 945 for controlling the transmission of analog output signals, such as IEGM signals output to an EKG machine or chart recorder.

Insofar as SCS is concerned, main CPU 902 includes an SCS baseline efficacy calibration controller 950 operative to generate baseline and/or target patterns, signals, characteristics or other parameters pertaining to nerve impulse signals or HRV signals or other suitable quantifiable parameters, particularly parameters associated with SCS of known efficacy. The baseline and/or target parameters are transmitted to (and then stored within) the pacer/ICD (or SCS device 18, or both) for use in controlling SCS.

Depending upon the implementation, the various components of the CPU may be implemented as separate software modules or the modules may be combined to permit a single module to perform multiple functions. In addition, although shown as being components of the CPU, some or all of these components may be implemented separately, using ASICs or the like. The descriptions provided herein with respect to FIG. 10 are intended merely to provide an overview of the operation of programmer and are not intended to describe in detail every feature of the hardware and software of the programmer nor to provide an exhaustive list of the functions performed by the programmer.

In general, while the invention has been described with reference to particular embodiments; modifications can be made thereto without departing from the scope of the invention. Note also that the term "including" as used herein is intended to be inclusive, i.e. "including but not limited to."

What is claimed is:

1. A method for use with an implantable medical system for implant within a patient, the method comprising:
   delivering neurostimulation to the patient using the implantable system;
   sensing spinal cord nerve impulse signals in response to the neurostimulation;
   measuring a power spectral density (PSD) parameter of a heart rate variability (HRV) parameter using a cardiac sensing lead implanted within the patient and assessing patient mood based on the PSD of the HRV;
   analyzing the spinal cord nerve impulse signals to determine whether the signals are indicative of effective neurostimulation sufficient to improve patient mood; and
   controlling the delivery of additional neurostimulation based on the spinal cord nerve impulse signals and the assessed patient mood based on the PSD of the HRV to adjust neurostimulation efficacy to improve patient mood.

2. The method of claim 1 wherein the implantable medical system includes a spinal cord stimulation (SCS) device and wherein the neurostimulation includes SCS and wherein controlling the delivery of additional neurostimulation includes adjusting SCS control parameters.

3. The method of claim 2 wherein SCS is delivered in accordance with a set of SCS control parameters including one or more of: a neuromodulation amplitude; a neuromodulation frequency; a neuromodulation pulse width; and a neuromodulation electrode configuration.

4. The method of claim 2 wherein sensing nerve impulse signals includes detecting one or more of afferent neural electrical signals and efferent neural electrical signals along at least one spinal cord fiber.

5. The method of claim 2 wherein sensing nerve impulse signals includes detecting signals within a passband in the range of 100 Hz to 2 kHz with a sampling frequency of at least 4 kHz.

6. The method of claim 2 wherein analyzing the nerve impulse signals to determine whether the impulse signals are indicative of effective neurostimulation to improve patient mood includes:
   determining nerve impulse firing parameters from the nerve impulse signals sensed within the patient;
   inputting one or more of baseline nerve impulse parameters and target nerve impulse parameters for the patient; and
   comparing the nerve impulse parameters determined for the patient to the input nerve impulse parameters to assess the efficacy of the SCS and quantify an improvement in patient mood.

7. The method of claim 6 wherein determining nerve impulse firing parameters includes determining one or more of: average firing rates, maximum firing rates, average firing intervals, maximum firing intervals, minimum firing intervals, firing rate variability, dominant frequency and bandwidth of dominant frequency.

8. The method of claim 6 wherein inputting nerve impulse parameters includes inputting target nerve impulse parameters known to be associated with one or the other of a positive patient mood and a negative patient mood.

9. The method of claim 6 wherein controlling the delivery of additional neurostimulation based on nerve impulse signals includes:
adjusting SCS control parameters to achieve nerve impulse parameters more closely corresponding to the target parameters associated with SCS known to be effective within the patient for improving patient mood; and
repeating the steps of delivering neurostimulation to the patient, sensing spinal cord nerve impulse signals, and analyzing the nerve impulse signals to determine whether the signals are associated with effective SCS for improving patient mood.

10. The method of claim 2 wherein adjusting the SCS control parameters includes adjusting one or more of: an SCS amplitude; an SCS frequency; an SCS pulse width; an SCS cycle time and an SCS electrode configuration.

11. The method of claim 2 further including controlling the delivery of additional SCS based, on cardiac electrical parameters measured using the cardiac sensing lead implanted within the patient.

12. The method of claim 11 for use with an implantable system also having a separate implantable cardiac rhythm management device and wherein the cardiac electrical parameters are measured by the cardiac rhythm management device for use in controlling the separate SCS device.

13. The method of claim 2 wherein the HRV PSD parameter includes one or more of a target PSD pattern indicative of a positive patient mood and a baseline PSD pattern indicative of a negative patient mood.

14. The method of claim 13 further including:
inputting one or more of a target HRV PSD pattern and a baseline HRV PSD pattern;
detecting a new HRV PSD pattern within the patient; and
comparing the new HRV PSD pattern to the input HRV PSD pattern to assess the efficacy of the SCS.

15. The method of claim 14 wherein controlling the delivery of additional SCS based, on HRV PSD includes:
adjusting SCS control parameters to achieve an HRV PSD pattern more closely corresponding to the target HRV PSD pattern indicative of positive patient mood; and
repeating the steps of delivering neurostimulation to the patient, detecting HRV PSD patterns in response to the neurostimulation and analyzing the HRV PSD patterns to determine whether the HRV PSD patterns are associated with positive patient mood.

16. The method of claim 1 for use with an implantable system also having a separate implantable cardiac rhythm management device and wherein at least one of the steps of sensing nerve impulse signals, analyzing the nerve impulse signals and controlling the delivery of additional neurostimulation are performed by the cardiac rhythm management device.

17. The method of claim 1 wherein controlling the delivery of additional neurostimulation to adjust neurostimulation efficacy is performed to improve one or more of antiarrhythmic and sympatholytic effects associated with the neurostimulation.

18. The method of claim 1 wherein assessing patient mood includes associating an increase in a peak frequency of the PSD with an improvement in patient mood.

19. An implantable medical system for implant within a patient, the system comprising:
a neurostimulation delivery system operative to deliver neurostimulation to the patient;
a spinal cord nerve impulse signal sensing system operative to sense spinal cord nerve impulse signals in response to the neurostimulation;
a detector operative to measure a power spectral density (PSD) of a heart rate variability (HRV) parameter using a cardiac sensing lead implanted within the patient and to assess patient mood based op the PSD of the HRV;
a spinal cord nerve impulse signals analysis system operative to analyze the spinal cord nerve impulse signals to determine whether the signals are indicative of effective neurostimulation sufficient to improve patient mood; and
a neurostimulation control system operative to control the delivery of additional neurostimulation based on the spinal cord nerve impulse signals and the assessed patient mood based on the PSD of the HRV to adjust neurostimulation efficacy to improve patient mood.

20. The implantable medical system of claim 19 wherein the system includes a spinal cord stimulation (SCS) system and a cardiac rhythm management device.

21. The system of claim 19 wherein the controller associates an increase in a peak frequency of the PSD with an improvement in patient mood.

22. A system for use with an implantable spinal cord stimulation (SCS) device for implant within a patient, the method comprising:
means for delivering neurostimulation to the patient using the implantable system;
means for sensing spinal cord nerve impulse signals in response to the neurostimulation;
means for measuring a power spectral density (PSD) of a heart rate variability (HRV) parameter using a cardiac sensing lead implanted within the patient and means for assessing patient mood based on the PSD of the HRV;
means for analyzing the spinal cord nerve impulse signals to determine whether the signals are indicative of effective neurostimulation sufficient to improve patient mood; and
means for controlling the delivery of additional neurostimulation based on the spinal cord nerve impulse signals and the assessment of patient mood based on the PSD of the HRV to adjust neurostimulation efficacy to improve patient mood.

23. The system of claim 22 wherein the means for assessing patient mood associates an increase in a peak frequency of the PSD with an improvement in patient mood.

24. A method for use with an implantable medical system that includes a spinal cord stimulation (SCS) device for implant within a patient, the method comprising:
delivering SCS to the patient using the implantable system;
sensing spinal cord nerve impulse signals in response to the SCS;
measuring cardiac electrical parameters using a sensing lead implanted within the patient, wherein the cardiac electrical parameters include heart rate variability (HRV) parameters including parameters representative of a power spectral density (PSD) of HRV and including one or more of a target PSD pattern indicative of a positive patient mood and a baseline PSD pattern indicative of a negative patient mood;
analyzing the spinal cord nerve impulse signals to determine whether the signals are indicative of effective SCS sufficient to improve patient mood; and
controlling the delivery of additional SCS based on the spinal cord nerve impulse signals and the target PSD pattern to adjust SCS efficacy to improve patient mood.

* * * * *